US008828001B2

(12) United States Patent
Stearns et al.

(10) Patent No.: US 8,828,001 B2
(45) Date of Patent: Sep. 9, 2014

(54) BONE DRILL AND METHODS OF TREATMENT

(75) Inventors: Stanley D. Stearns, Gig Harbor, WA (US); H. Max Loy, Jr., Houston, TX (US)

(73) Assignee: Gabriel Institute, Inc., Houston, TX (US)

( * ) Notice: Subject to any disclaimer, the term of this patent is extended or adjusted under 35 U.S.C. 154(b) by 1578 days.

(21) Appl. No.: 12/064,276

(22) PCT Filed: Feb. 15, 2008

(86) PCT No.: PCT/US2008/054085
§ 371 (c)(1),
(2), (4) Date: Feb. 20, 2008

(87) PCT Pub. No.: WO2008/103606
PCT Pub. Date: Aug. 28, 2008

(65) Prior Publication Data
US 2010/0256644 A1    Oct. 7, 2010

Related U.S. Application Data

(60) Provisional application No. 60/890,831, filed on Feb. 20, 2007, provisional application No. 60/891,183, filed on Feb. 22, 2007.

(51) Int. Cl.
*A61B 17/16* (2006.01)
*A61B 17/00* (2006.01)
*A61B 17/34* (2006.01)

(52) U.S. Cl.
CPC ....... *A61B 17/1642* (2013.01); *A61B 2017/003* (2013.01); *A61B 17/3472* (2013.01)
USPC .......................... 606/80; 408/115 B; 408/127

(58) Field of Classification Search
CPC ........... A61B 17/1631; A61B 17/1633; A61B 17/1642
USPC ........................ 606/79–81, 180; 433/144, 165
See application file for complete search history.

(56) References Cited

U.S. PATENT DOCUMENTS 550,783 A * 12/1895 Elliott et al. .................... 175/75
1,630,239 A    5/1924 Binley et al.
(Continued)

FOREIGN PATENT DOCUMENTS

WO    2008103606 A2    8/2008

OTHER PUBLICATIONS

Thomas Dunn, International Preliminary Report on Patentability, Aug. 7, 2009, 7 pages, United States Patent and Trademark Office as International Preliminary Examining Authority, Alexandria, Virginia, US.

(Continued)

*Primary Examiner* — Michael T Schaper
(74) *Attorney, Agent, or Firm* — Crain, Caton & James, P.C.; James E. Hudson, III

(57) ABSTRACT

A minimally invasive and particularly small apparatus for drilling into bone and for providing for delivery of medical treatment is provided. The directional drilling apparatus includes a miniature shaft, a bit, first shaft-mounted thrust ring, second shaft-mounted thrust ring, a tubing jacket surrounding the shaft and intermediate the first and second shaft-mounted thrust rings, and a guide tube encapsulating the tubing jacket. As a result, a hole, targeted towards a cancerous lesion within the bone, is possible. After removal of the shaft and the tubing jacket, treatment may be introduced through the particularly small passage created by the directional drilling apparatus or through the passage via a capillary inserted through at least a portion of the guide tube and the passage, which guide tube may include a hypodermic needle.

20 Claims, 10 Drawing Sheets

(56) References Cited

U.S. PATENT DOCUMENTS

| | | | |
|---|---|---|---|
| 2,958,349 A * | 11/1960 | McNutt | 408/67 |
| 2,960,892 A * | 11/1960 | Spravka | 408/127 |
| 3,016,073 A * | 1/1962 | Broussard et al. | 408/85 |
| 3,388,505 A * | 6/1968 | Dreiling | 451/180 |
| 3,617,143 A * | 11/1971 | McKee | 408/127 |
| 4,265,231 A | 5/1981 | Scheller, Jr. et al. | |
| 4,541,423 A * | 9/1985 | Barber | 606/80 |
| 4,941,466 A | 7/1990 | Romano | |
| 5,002,546 A | 3/1991 | Romano | |
| 5,017,057 A * | 5/1991 | Kryger | 408/68 |
| 5,387,218 A | 2/1995 | Meswania | |
| 5,395,188 A * | 3/1995 | Bailey et al. | 408/127 |
| 5,509,918 A | 4/1996 | Romano | |
| 5,569,197 A | 10/1996 | Helmus et al. | |
| 5,700,265 A | 12/1997 | Romano | |
| 5,709,511 A * | 1/1998 | Esmailzadeh | 409/199 |
| 5,772,661 A | 6/1998 | Michelson | |
| 5,779,708 A | 7/1998 | Wu | |
| 5,928,241 A * | 7/1999 | Menut et al. | 606/80 |
| 6,018,094 A * | 1/2000 | Fox | 606/191 |
| 6,039,127 A | 3/2000 | Myers | |
| 6,257,808 B1 * | 7/2001 | Groot | 408/1 R |
| 6,309,396 B1 * | 10/2001 | Ritland | 606/96 |
| 6,322,565 B1 | 11/2001 | Garner et al. | |
| 6,391,017 B2 | 5/2002 | Bays | |
| 6,511,266 B1 * | 1/2003 | Groot | 408/1 R |
| 6,740,090 B1 * | 5/2004 | Cragg et al. | 606/79 |
| 6,790,210 B1 * | 9/2004 | Cragg et al. | 606/80 |
| 6,818,001 B2 * | 11/2004 | Wulfman et al. | 606/159 |
| 7,066,942 B2 | 6/2006 | Treace | |
| 7,488,322 B2 * | 2/2009 | Brunnett et al. | 606/79 |
| 7,569,056 B2 * | 8/2009 | Cragg et al. | 606/79 |
| 7,604,636 B1 * | 10/2009 | Walters et al. | 606/80 |
| 8,251,999 B2 | 8/2012 | Stearns et al. | |
| 2003/0032939 A1 | 2/2003 | Gibbs | |
| 2003/0130664 A1 | 7/2003 | Boucher et al. | |
| 2003/0220646 A1 * | 11/2003 | Thelen et al. | 606/79 |
| 2004/0220577 A1 * | 11/2004 | Cragg et al. | 606/80 |
| 2005/0236189 A1 * | 10/2005 | Rankin, III | 175/73 |
| 2005/0267481 A1 * | 12/2005 | Carl et al. | 606/79 |
| 2006/0067883 A1 | 3/2006 | Krom et al. | |
| 2006/0206131 A1 | 9/2006 | Conquergood et al. | |
| 2006/0241630 A1 * | 10/2006 | Brunnett et al. | 606/80 |
| 2006/0264896 A1 | 11/2006 | Palmer | |
| 2006/0264957 A1 * | 11/2006 | Cragg et al. | 606/80 |
| 2007/0055259 A1 * | 3/2007 | Norton et al. | 606/79 |
| 2007/0093840 A1 * | 4/2007 | Pacelli et al. | 606/80 |
| 2007/0196275 A1 | 8/2007 | Li et al. | |
| 2007/0231329 A1 | 10/2007 | Lazar et al. | |
| 2008/0154275 A1 | 6/2008 | Assell et al. | |
| 2009/0187191 A1 * | 7/2009 | Carl et al. | 606/80 |
| 2009/0228014 A1 | 9/2009 | Stearns et al. | |

OTHER PUBLICATIONS

Young, Lee W., International Search Report—PCT/US08/02026, Jun. 11, 2008, 2 pages, United States Patent and Trademark Office as International Search Authority, Alexandria, Virginia, US.

Young, Lee W., Written Opinion of the ISA—PCT/US08/02026, Jun. 11, 2008, 6 pages, United States Patent and Trademark Office as International Search Authority, Alexandria, Virginia, US.

Lee W. Young, International Search Report—PCT/US08/54085, Aug. 7, 2008, 2 pages, United States Patent and Trademark Office as International Search Authority, Alexandria, Virginia US.

Lee W. Young, International Search Report—PCT/US08/54085, Aug. 7, 2008, 6 pages, United States Patent and Trademark Office as International Search Authority, Alexandria, Virginia, US.

Thomas Dunn, Notification of Transmittal of International Preliminary Report on Patentability, Aug. 10, 2009, 2 pages, United States Patent and Trademark Office as International Preliminary Examining Authority, Alexandria, Virginia, US.

Thomas Dunn, International Preliminary Report on Patentability, Aug. 7, 2009, 2 pages, United States Patent and Trademark Office as International Preliminary Examining Authority, Alexandria, Virginia, US.

Nicholas W. Woodall, Office Action of Jan. 18, 2012—U.S. Appl. No. 12/437,910, Jan. 18, 2012, 10 pages, United Patent & Trademark Office, Alexandria, Virginia, USA.

Linda Sholl, International Preliminary Report on Patentability—PCT/US10/33511 and Notification of Transmittal, May 25, 2011, 7 pages, United States Patent & Trademark Office as Examining Authority, Alexandria, Virginia, USA.

Blaine R. Copenheaver, International Search Report—PCT/US10/33511, Jul. 13, 2010, 2 pages, United States Patent & Trademark Office as Examining Authority, Alexandria, Virginia, USA.

Blaine R. Copenheaver, Written opinion—PCT/US10/33511, Jul. 13, 2010, 4 pages, United States Patent & Trademark Office as Examining Authority, Alexandria, Virginia, USA.

Nicholas W Woodall, Non-Final Office Action, U.S. Appl. No. 12/437,910, Apr. 6, 2012, 31 pages, United States Patent and Trademark Office, Alexandria, United States.

Nicholas W. Woodall, Notice of Allowance—U.S. Appl. No. 12/437,910, Jun. 11, 2012, 7 pages, United States Patent and Trademark Office, Alexandria, Virginia, US.

Lee W. Young, International Preliminary Report on Patentability—PCT/US08/02026, Nov. 8, 2010, 3 pages, United States Patent and Trademark Office as International Search Authority, Alexandria, Virginia, US.

* cited by examiner

BONE DRILL AND METHODS OF TREATMENT

CROSS REFERENCE TO RELATED APPLICATIONS

The priority of PCT Application No. PCT/US2008/054085, filed on Feb. 15, 2008, is hereby claimed, and the specification thereof is incorporated herein by reference. PCT Application No. PCT/US2008/054085 claims the benefit of U.S. Provisional Patent Application No. 60/890,831 entitled, "Directional Bone Drilling and Methods of Treatment" filed on Feb. 20, 2007 in the United States Patent and Trademark Office and U.S. Provisional Patent Application No. 60/891,183 entitled, "Directional Bone Drilling and Methods of Treatment" filed on Feb. 22, 2007 in the United States Patent and Trademark Office, and both specifications thereof are incorporated herein by reference.

STATEMENT REGARDING FEDERALLY SPONSORED RESEARCH OR DEVELOPMENT

Not applicable.

BACKGROUND OF THE INVENTION

1. Field of Invention

The present invention relates to an apparatus to provide delivery of medical treatment to and within tissue or bone. In particular the present invention related to a minimally invasive and particularly small treatment delivery system including a drill and treatment delivery passage. Additionally, the present invention relates to a minimally invasive and particularly small apparatus for drilling of passages in bone for other purposes, such as the imposition of screws or other devices to fix a bone or bone portion in position.

2. Description of the Related Art

Delivery of medical treatments to tissue within bone is particularly difficult. Historically treatment has been delivered through the entire body in sufficient application amounts to ensure the necessary treatment amount reaches the tissue within the bone. As can be expected, this requires application amounts far in excess of the treatment amount necessary and can result in damage to other parts of the body as well as increased costs. Various solutions have been developed to attempt to reduce the application amount, typically by attempting to isolate the affected area from the body, including shunting of blood flow in the affected limb through a heart/lung machine to allow continued circulation within the limb while isolating the blood flow from the rest of the body. Similarly accessing bone to directly apply any treatment amount or to drill into the bone, such as drilling a passage for screws to fix a bone or bone particle in position, has historically been quite difficult and invasive. Moreover, such passages have generally been no smaller than 0.15875 cm (0.0625 inches). Likewise, drilling such passages has resulted in significant fracturing of the bone itself The need therefore exists for apparatus to provide delivery of medical treatment to and within bone which permits direct application of only the necessary treatment amount and for a system to access bone to directly apply any treatment amount or to drill into the bone such as drilling a passage for screws to fix a bone or bone particle in position, with minimal invasion. A need further exists for an apparatus which may be used with tissue rather than bone.

Such a need may be particularly important in the treatment of osteosarcoma and similar cancers of bone.

BRIEF SUMMARY OF THE INVENTION

The present invention overcomes the foregoing drawbacks of previous systems.

The present invention provides an improved apparatus to provide delivery of medical treatment to tissue, which may be within a bone, specifically by providing an improved drill. The directional drilling apparatus includes a miniature shaft, a bit, first shaft-mounted thrust ring, second shaft-mounted thrust ring, a tubing jacket surrounding the shaft and intermediate the first and second shaft-mounted thrust rings, and a guide tube encapsulating the tubing jacket. The guide tube may be straight or may have a curvature at the end where the guide tube contacts or is very close proximity to the bone, so that as the bit rotates and is advanced from the guide tube, the shaft and tubing jacket are deformed consistent with the guide tube. As a result, straight or curved holes may be drilled, targeted towards a cancerous lesion within the tissue within the bone. The guide tube may comprise, in part, a hypodermic needle.

After removal of the directional drilling apparatus, treatment may be introduced through the particularly small hole created by the directional drilling apparatus. Due to the small diameter of the tubing jacket and the drill, the drill is particularly small, such as 0.04318 cm (0.017 inches).

When the guide tube includes a hypodermic needle, the drill bit, shaft, tubing jacket, and a portion of the guide tube other than the hypodermic needle may be removed after the hole has been drilled, and a capillary inserted through the hypodermic needle portion of the guide tube to the tissue to be treated.

In another aspect of the present invention, the present invention provides an improved method of delivering medical treatment to and into bone.

In another aspect of the present invention, by using a very smooth bore tube to guide a flexible drill hard enough to cut through the bone, but not likely to break-off with the bone or to fracture the bone, provided with a relatively short cutting tip compared to the length of the overall tool, a drilling apparatus is provided capable of drilling directly, angled or even curved passages through bone to access the cancerous lesion from inside the bone without deleterious affects on the patient.

The foregoing and other objectives, features, and advantages of the invention will be more readily understood upon consideration of the following detailed description of the invention, taken in conjunction with the accompanying drawings.

BRIEF DESCRIPTION OF THE SEVERAL DRAWINGS

So that the manner in which the described features, advantages and objects of the invention, as well as others which will become apparent, are attained and can be understood in detail, more particular description of the invention briefly summarized above may be had by reference to the embodiments thereof that are illustrated in the drawings, which drawings form a part of this specification. It is to be noted, however, that the appended drawings illustrate only typical preferred embodiments of the invention and are therefore not to be considered limiting of its scope as the invention may admit to other equally effective embodiments.

DETAILED DESCRIPTION OF THE INVENTION

The invention may be further understood by the following non-limiting examples. Although the description herein contains many specificities, these should not be construed as limiting the scope of the invention but as merely providing illustrations of some of the presently preferred embodiments of the invention. For example, thus the scope of the invention should be determined by the appended claims and their equivalents, rather than by the examples given. In general the terms and phrases used herein have their art-recognized meaning, which can be found by reference to standard texts, journal references and contexts known to those skilled in the art. The following definitions are provided to clarify their specific use in the context of the invention. All references cited herein are hereby incorporated by reference to the extent not inconsistent with the disclosure herewith.

Figure 1:
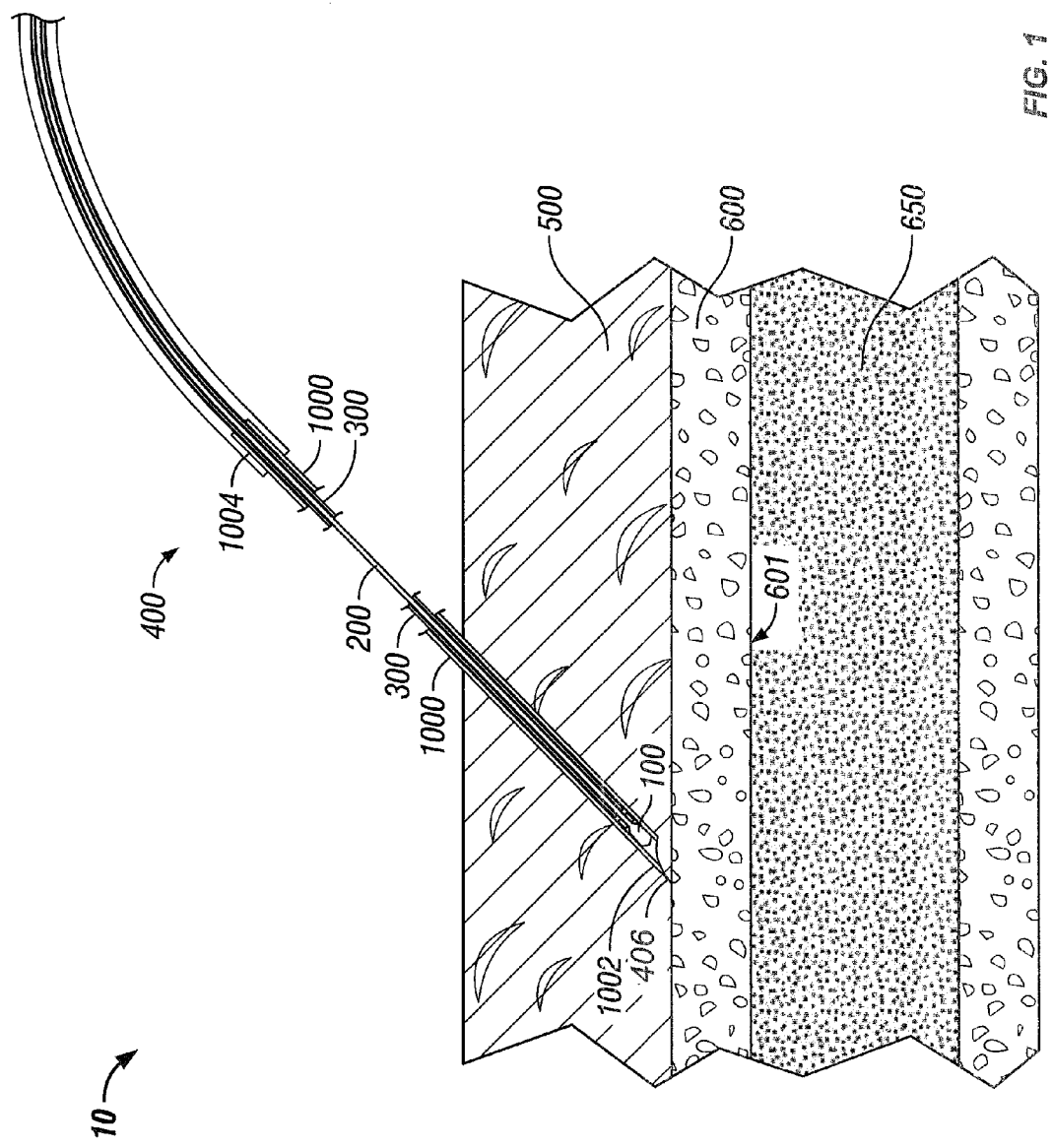
FIG. 1 illustrates a side view of the preferred embodiment of the present invention in relation to the bone.
Figure 2:
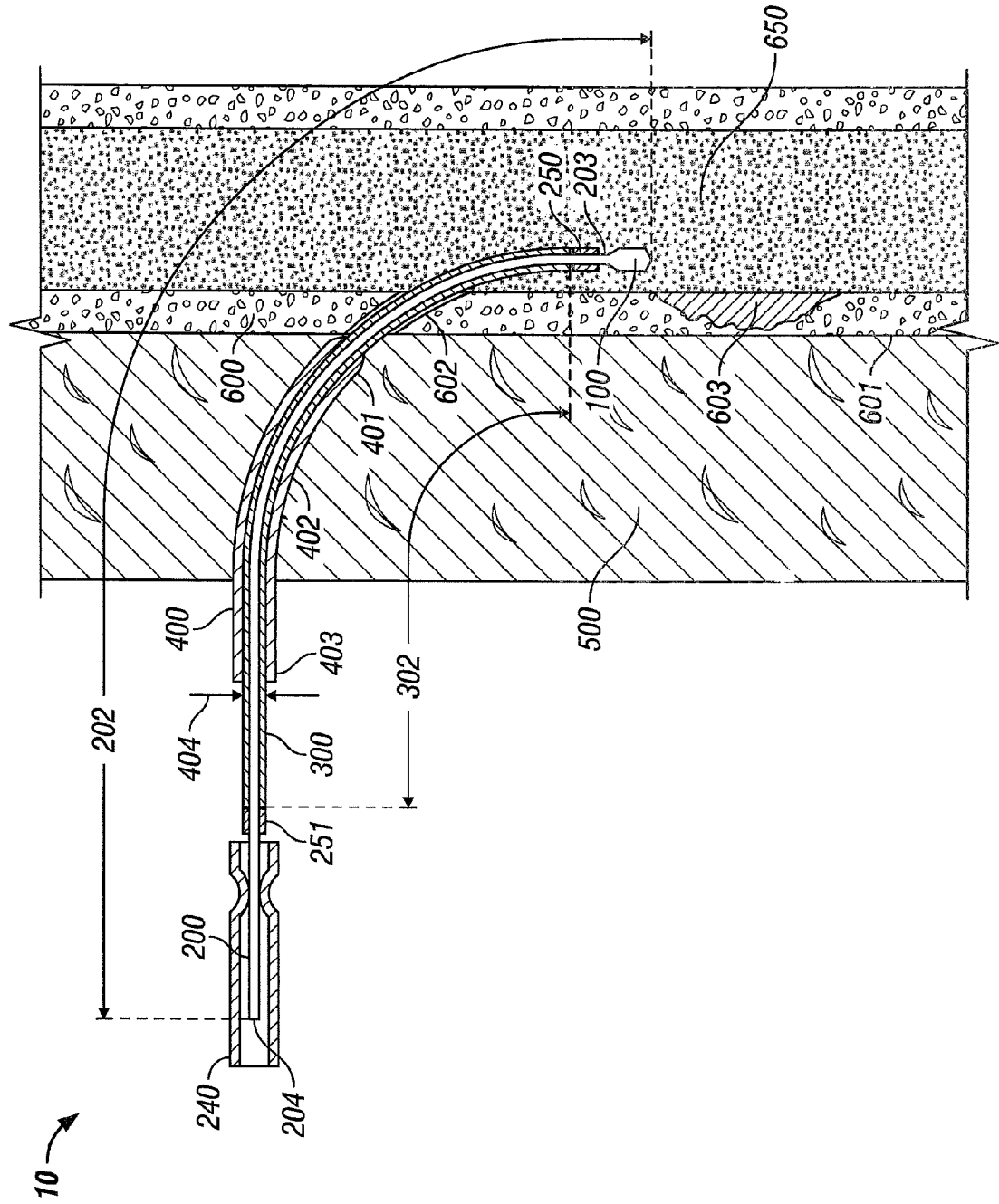
FIG. 2 illustrates a side view of an alternative embodiment of the present invention in relation to the cancerous lesion to be treated and the associated bone.

Referring to the FIG. 1 and FIG. 2, a directional drilling apparatus 10, for drilling into a bone 600 is shown. Likewise, drilling apparatus may be used to drill into other body tissues. The directional drilling apparatus includes a bit 100, a shaft 200 a tubing jacket 300, and a guide tube 400. Referring to FIG. 2, drilling apparatus also includes a first thrust ring 250 and a second thrust ring 251. Guide tube 400 may be straight, as depicted in FIG. 1, or curved, as depicted in FIG. 2.

Figure 3:
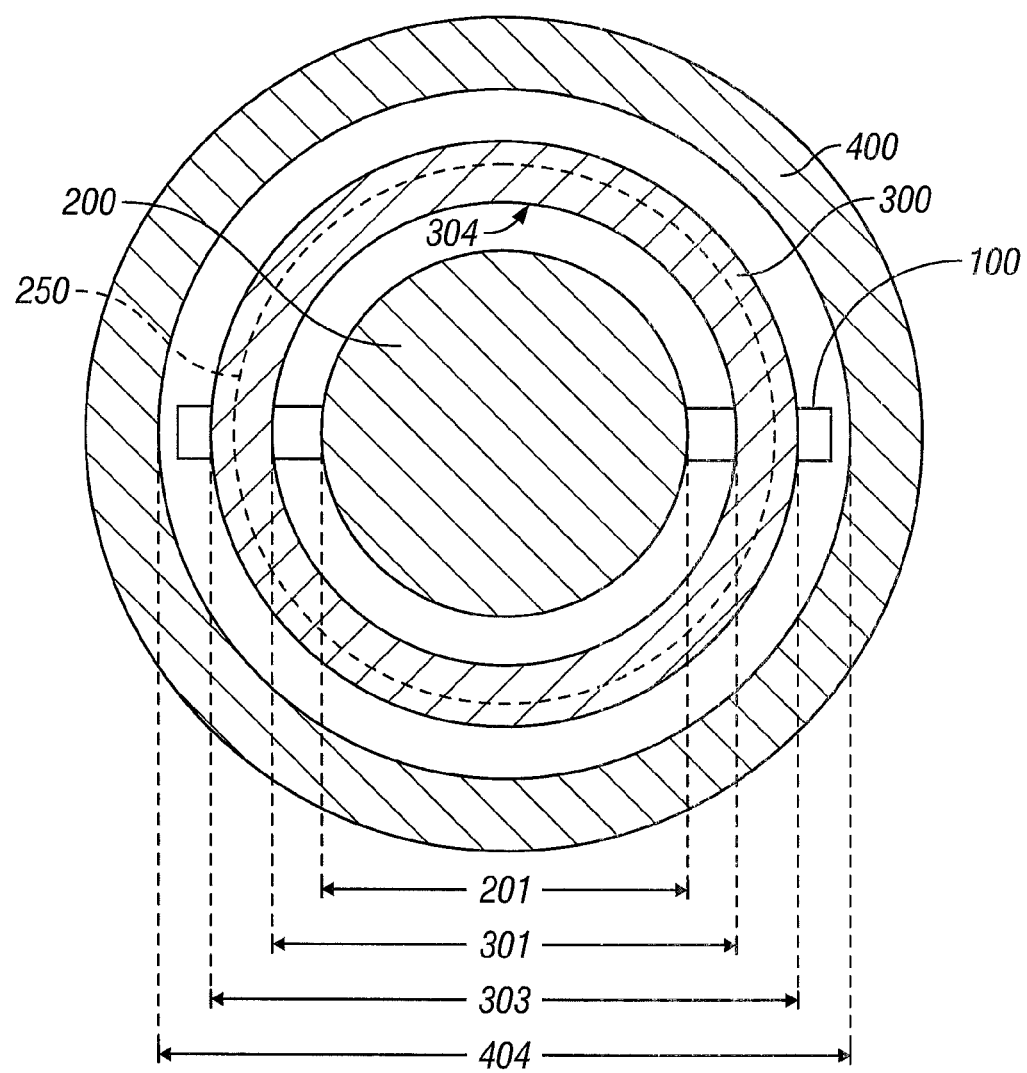
FIG. 3 illustrates a cross sectional view of the present invention showing the relation of the shaft, tubing jacket and guide tube.

Referring to FIG. 3, in the preferred embodiment the tubing jacket 300 is particularly small compared to the bone to be drilled or the body to be entered. The inner diameter 301 of the tubing jacket may be in the area of 0.0254 cm (0.010 inches). The tubing jacket 300 may be formed by electroplating nickel over a diamond-drawn mandrel in a continuous process. Formation of a tubing jacket 300 by such method provides the inner surface 304 of the tubing jacket 300 with a resulting 0.00000254-0.00000508 cm (1-2microinch) finish. This mirror-like interior means that the tubing jacket 300 has a precise interior finish and creates minimum friction with the shaft 200.

A shaft 200, having an outer diameter 201 slightly sufficiently smaller than the inner diameter 301 of the tubing jacket 300, is inserted through the tubing jacket 300. The mandrel used to form the tubing jacket 300 may be retained as the shaft 200. Alternatively, any ductile rod having an outer diameter 201 smaller than the inner diameter 301 of the tubing jacket 300 may be used. The shaft 200 therefore has a quite small outer diameter. In the preferred embodiment, the outer diameter 201 of the shaft 200 is in the area of 0.02286 cm (0.009 inches).

Figure 4:
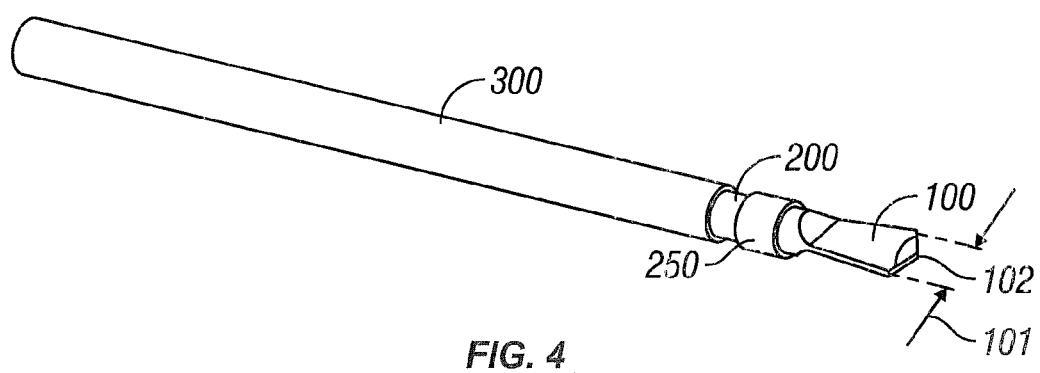
FIG. 4 illustrates an isometric view of the present invention, providing a better image of the bit, thrust ring, and tubing jacket.
Figure 5:
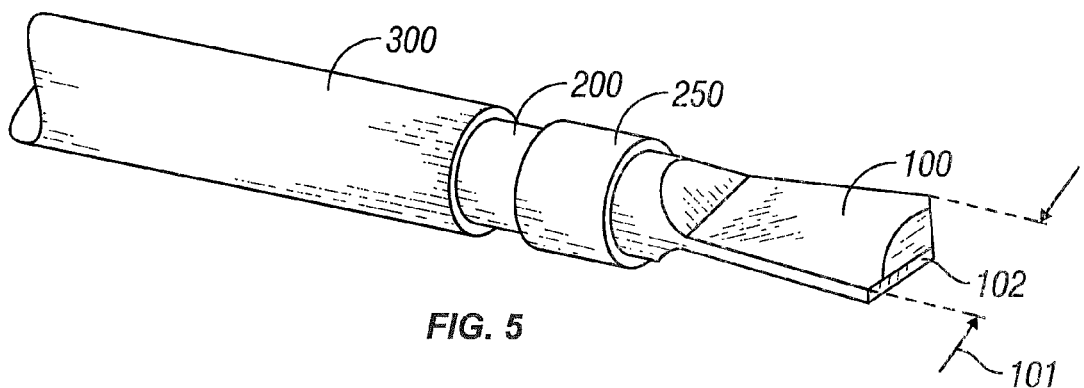
FIG. 5 illustrates a magnified isometric view of the bit, thrust ring, and tubing jacket.

Referring to FIG. 2, the shaft 200 has a length 202 longer than the length 302 of the tubing jacket 300. Referring to FIG. 4, and FIG. 5, a portion of the shaft 200 proximate the first end 203 may be flattened and honed to produce a bit 100, which may be a spade drill bit. Different bits, such as spherical, helical twist, or burr cutting tips, may alternatively be used.

Unlike standard drill bits, which have high strength and brittleness, the bit 100 is quite ductile. As can be appreciated, the loss of such a drill bit, likely with a brittle drill bit, in the body is to be avoided.

Referring to FIG. 4 and FIG. 5, the bit 100 has a width 101 greater than the outer diameter 303 of the tubing jacket 300, such that the tubing jacket 300 may follow through the passage precisely carved by the bit 100. The bit 100 also has a drill point or cutting edge 102.

Referring to FIG. 4 and FIG. 5, a first thrust ring 250 may be affixed at the junction of the bit 100 and the shaft 200, or to the shaft 200 at any location near the first end 203 of the shaft 200, to provide a surface against which the tubing jacket 300 may be retained during withdrawal of the shaft 200. Referring to FIG. 2, a second thrust ring 251 may be affixed to the shaft 200. A second thrust ring 251 supplies a surface to retain the tubing jacket 300 during linear movement of the shaft 200 and the bit 100 into the bone 600 and/or into tissue.

Referring to FIG. 3, thrust rings 250 and 251 each have an outer diameter greater than the shaft outer diameter 201 but less than or equal to, i.e. not greater than, the tubing jacket outer diameter 303.

Referring again to FIG. 2, the shaft 200 is connected to a motor or other radial and linear driver to rotate the shaft 200 in operation. The shaft 200 may be affixed or connected to a larger outer diameter drive tube 240 to provide for application of rotational and linear force. The drive tube 240 may thereby enclose the shaft 200 at its shaft second end 204.

Referring to FIG. 1 and FIG. 2, a guide tube 400 surrounds the tubing jacket 300 and provides support for the tubing jacket 300. Referring to FIG. 2, in operation the guide tube 400 is placed in abutment or proximate to the bone 600 at its first end 401. The drilling apparatus 10 may be delivered directly to the bone or tissue to be drilled by using a hypodermic needle as part of the guide tube 400. Alternatively, the drilling apparatus 10 may be placed adjacent or proximate the bone 600 after site preparation, which may include surgical relocation of intermediate parts of the body 500, such as muscle and blood vessels.

Figure 6:
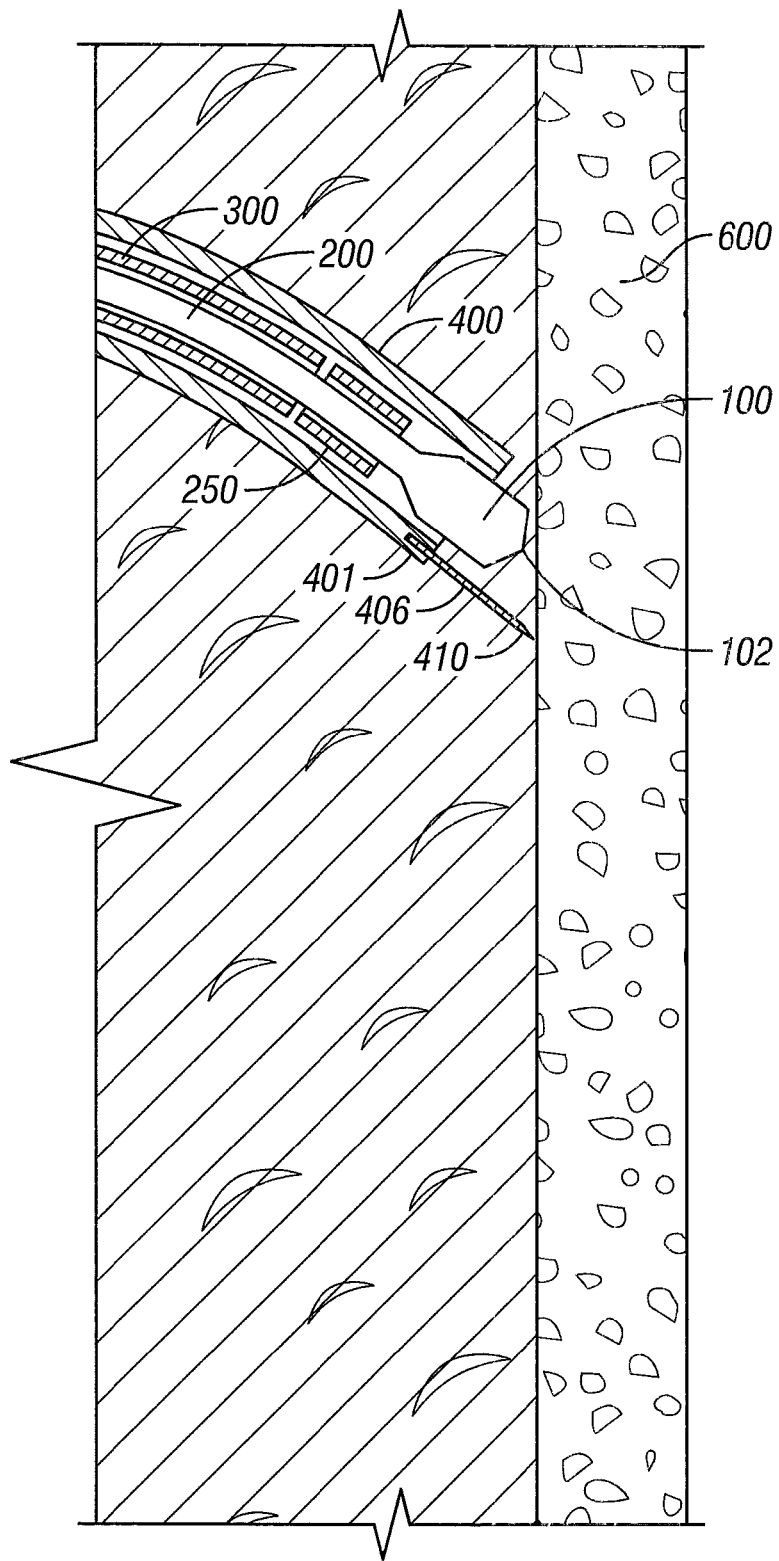
FIG. 6 illustrates a magnified side view of the point of contact between the alternative embodiment of the present invention and the associated bone.

Referring to FIG. 1 and FIG. 6, the guide tube 400 may include at least one prong 406 extending from the guide tube first end 401 to its sharp end 410. The length of the prong 406 is sufficient to achieve a desired angle of drilling while the sharp end 410 contacts the bone 600 and prevents the cutting tip 102 from contacting the bone 600 prior to advancing the cutting bit 100. Prong 406 is sized to ensure contact between the guide tube 400 and the bone 600 before the cutting bit 100 begins cutting into the bone 600 at the desired angle of attack.

Referring to FIG. 1 and FIG. 6, by virtue of the prong sharp end 410, prong 406 contacts the bone 600, or tissue on the surface of the bone 600, and becomes stationary, thereby preventing the cutting bit 100 from walking away from the point of its initial contact with the bone 600 or tissue on the surface of the bone 600. Moreover, as the prong 406 provides a limited point of contact between the bone 600 and the guide tube 400, any chips of bone 600 created by the cutting bit 100 are not trapped adjacent to the cutting bit 100 but rather may escape the passage 602, depicted in FIG. 8 and FIG. 10, created by the cutting bit 100. In the preferred embodiment, depicted in FIG. 1, the guide tube 400 is constructed to include a hypodermic needle 1000, with a prong 406 provided by the penetrating tip of the needle 1000.

Figure 7:
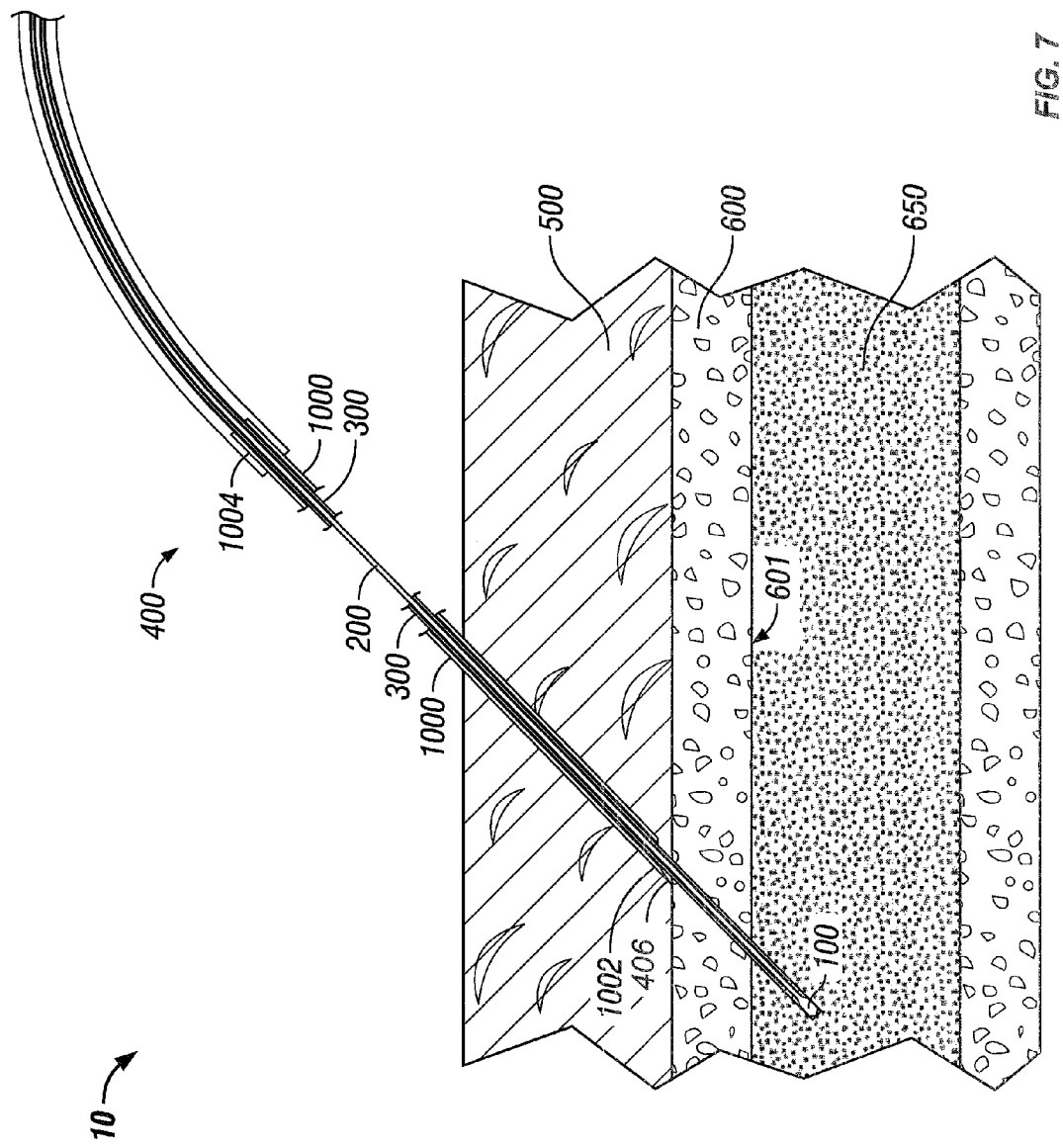
FIG. 7 illustrates a side view of the preferred embodiment of the present invention in relation to the bone during operation of the drill bit.
Figure 8:
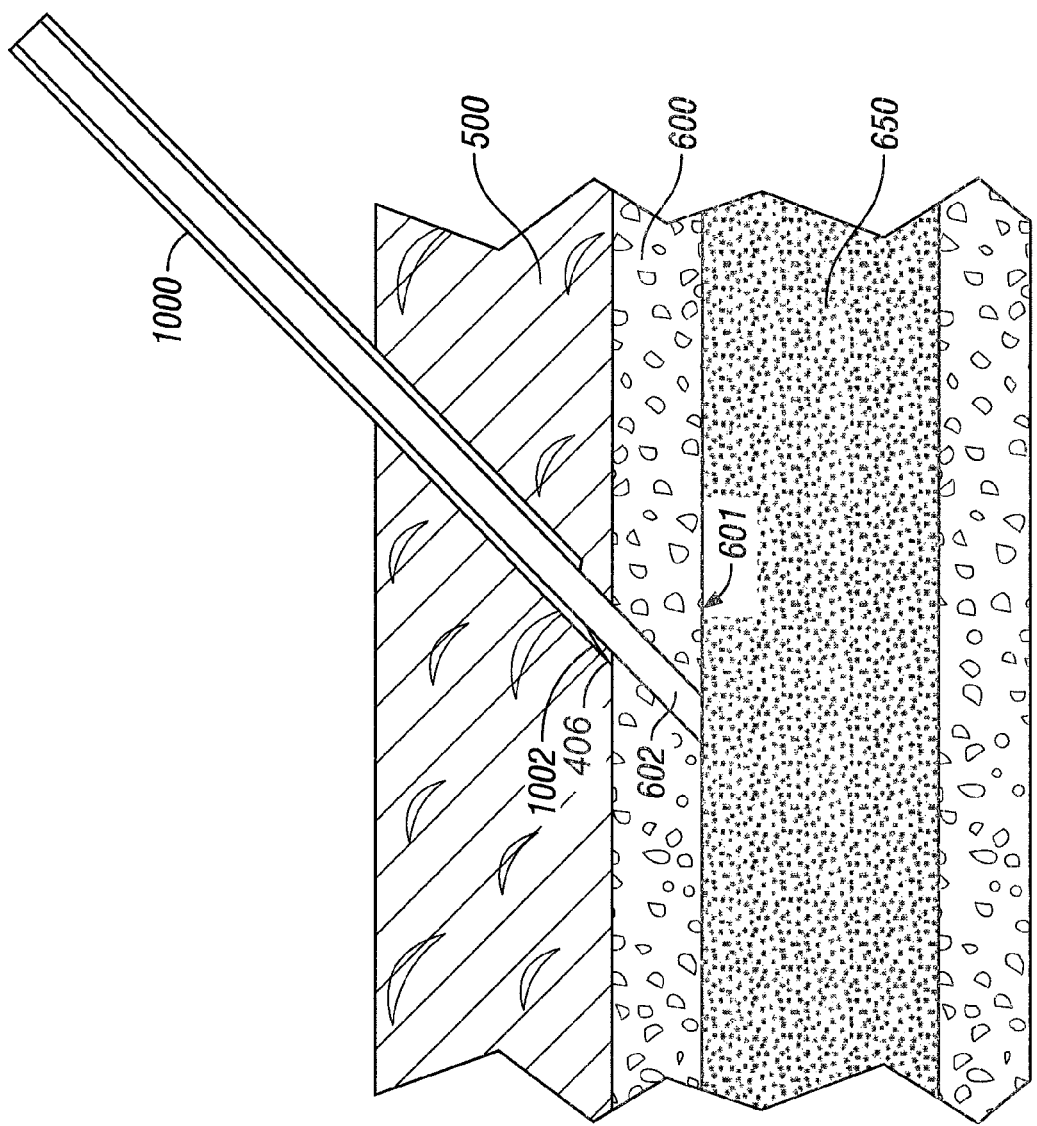
FIG. 8 illustrates a side view of the preferred embodiment of the present invention in relation to the bone after removal of all but the hypodermic needle.
Figure 9:
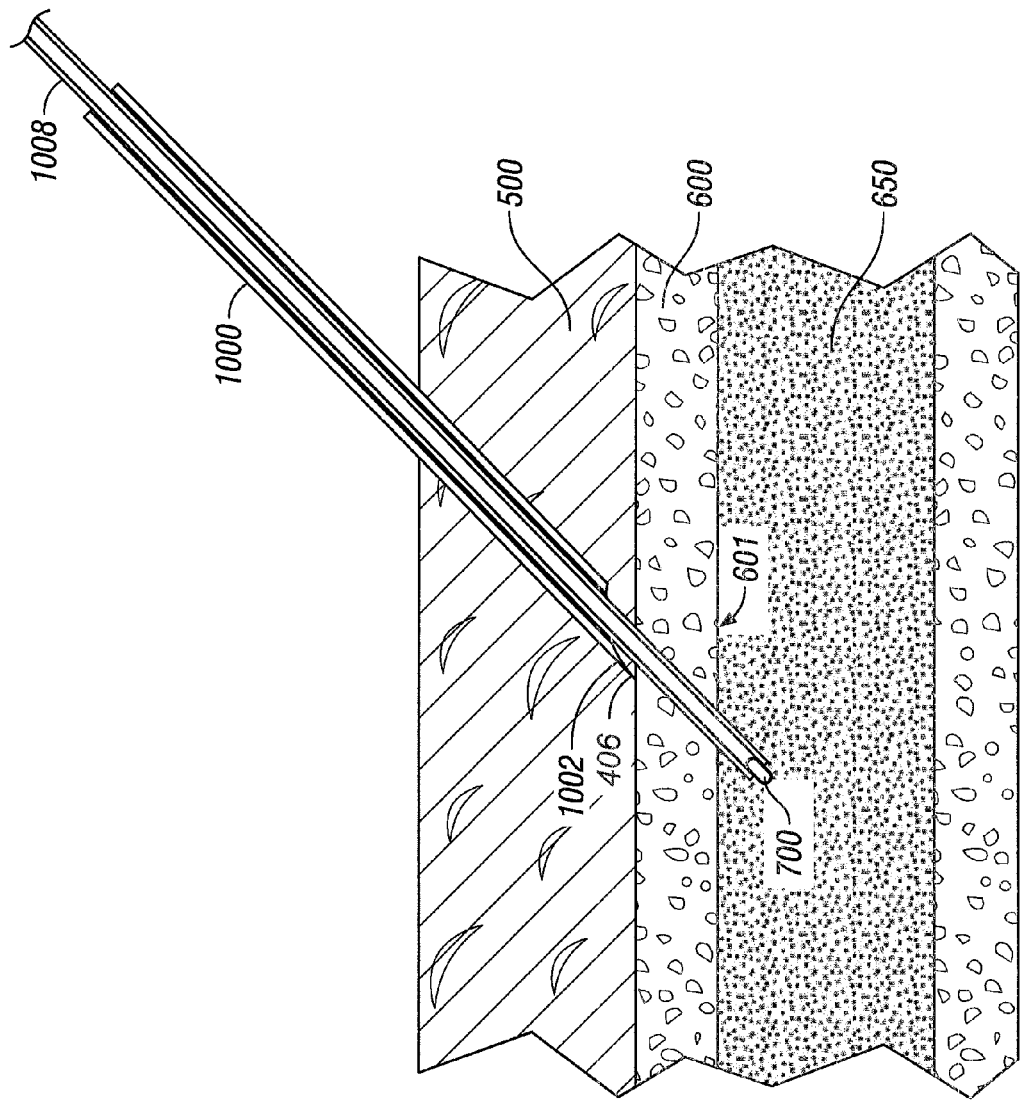
FIG. 9 illustrates a side view of the preferred embodiment of the present invention in relation to the bone after insertion of the capillary through the hypodermic needle and into the bone.

Referring to FIG. 1, FIG. 7, FIG. 8, and FIG. 9, use of a hypodermic needle 1000 as a portion of the guide tube 400 is illustrated. Referring to FIG. 1, the hypodermic needle 1000 fits within a counterbore of a guide tube section 1004, which thereby provides stability and a guide for tubing jacket 300 and shaft 200. The hypodermic needle 1000 includes a penetrating tip 1002, constructed to pierce tissue and including a prong 406. In operation, the hypodermic needle 1000 is pushed through the body 500 until contacting the bone 600, particularly so that the penetrating tip 1002 is in contact with bone and the prong 406 has sufficiently contacted the bone 600. Referring to FIG. 7, directional drilling apparatus 10 is then driven so that the bit 100 is rotated against the bone 600, while the shaft 200 is advanced, cutting through the bone wall 601, until reaching the marrow 650 and creating a passage 602. Referring to FIG. 8, the bit 100, the shaft 200, and the tubing jacket 300 are then withdrawn from the hypodermic needle 1000 section of guide tube 400, and the guide tube section 1004 is disengaged from hypodermic needle 1000, thus leaving only the hypodermic needle 1000 in contact with bone 600. Referring to FIG. 9, a capillary 1008 is then inserted into the hypodermic needle 1000, through the bone 600 via the passage 602, and into the marrow 650, permitting delivery of the treatment 700. Once the capillary 1008 is properly positioned, the hypodermic needle 1000 may be withdrawn up capillary 1008, but need not be.

Figure 10:
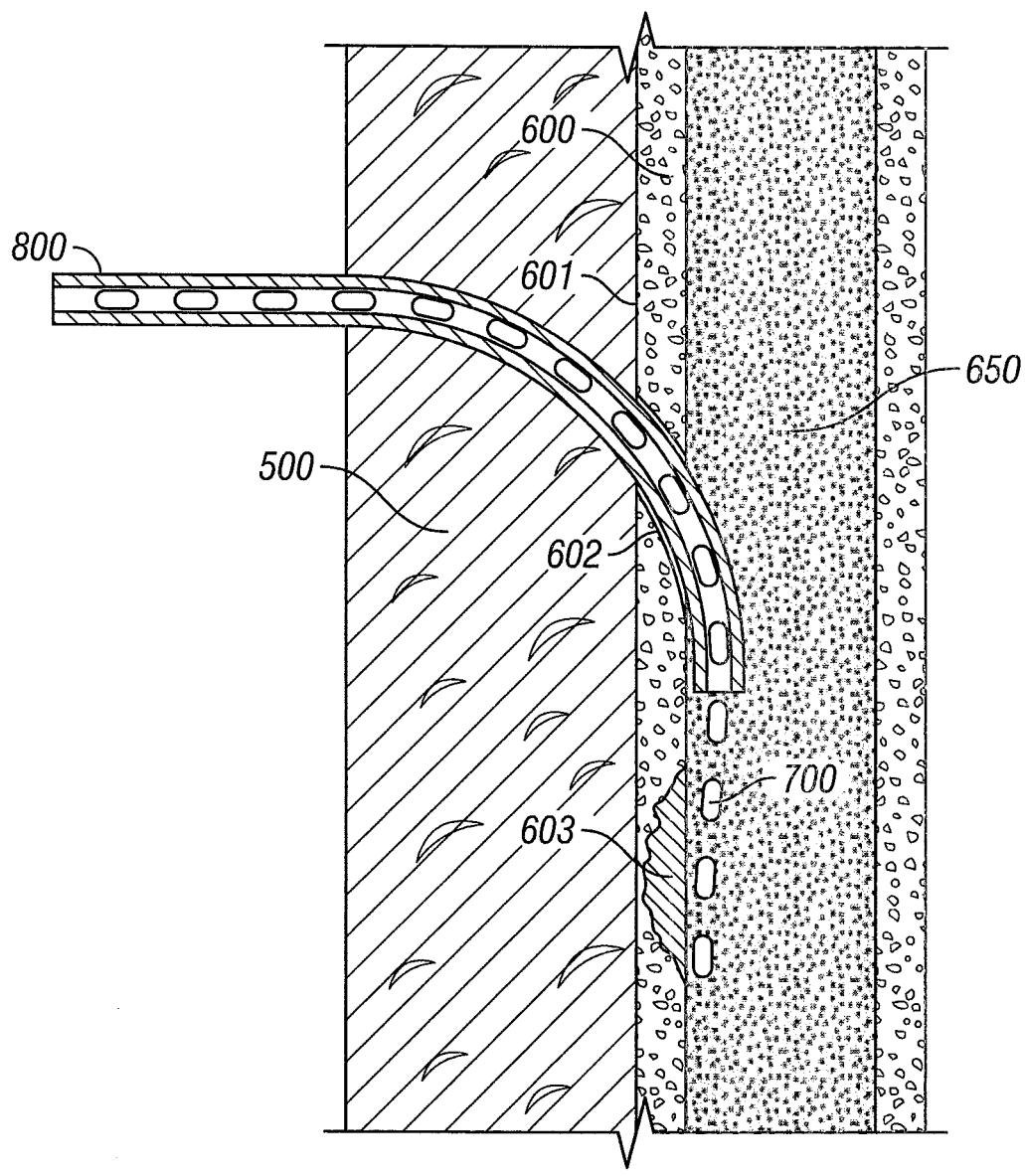
FIG. 10 illustrates a side view of the use of a treatment delivery system after removal of the invention.

In an alternative embodiment in FIG. 2, the guide tube 400 may include a first end 401 with a curvature 402, such that when the shaft 200, along with the tubing jacket 300, passes through the first end 401 of the guide tube 400, the shaft 200 and the tubing jacket 300 are deformed to the curvature 402 of the first end 401 of the guide tube 400. By virtue of this curvature 402, the drill bit 100 drills at a continuous curvature and thereby provides a passage 602 curved into and through the bone 600. Moreover, by virtue of this curvature 402 of the guide tube 400, the tubing jacket 300 may be driven linearly into the bone 600, but is curved at the point of contact by the guide tube 400. Alternatively, the guide tube 400 need not have a curvature 402 and may instead be straight, such that a straight hole may be drilled. The tubing jacket 300 has no rotation while moving through the bone 600, thereby inducing little or no damage to the surrounding bone 600 and marrow 650 due to the rotational forces of the shaft 200. By virtue of the curvature 402 of the guide tube 400, where a curved guide tube 400 is used, as the shaft 200 and the tubing jacket 300 are deformed into the curvature 402, thus driving the bit 100 into the bone 600 at the curvature 402. By virtue of the curvature 402 of the guide tube 400, it is not necessary to aim the guide tube 400 on the exterior of the bone 600 directly towards the cancerous lesion 603. Referring to FIG. 10, the drilling apparatus 10 may be removed and replaced with a treatment delivery system 800. The treatment 700 may be introduced through the marrow 650 toward the cancerous lesion 603 through the treatment delivery system 800.

The bone 600 is relatively soft when drilled in this manner, thus the drilling apparatus 10 is capable of drilling through the bone 600 without deleterious effects on the surrounding bone. Moreover, the drilling apparatus 10 produces a uniform, clean and particularly small diameter passage 602 through the bone 600. As a result of the small passage 602 directed toward the cancerous lesion 603 any of the various treatments known in the art, such as chemotherapy, radiochemical therapy, directed energy, may be provided without damage of adjacent tissue.

Figure 11:
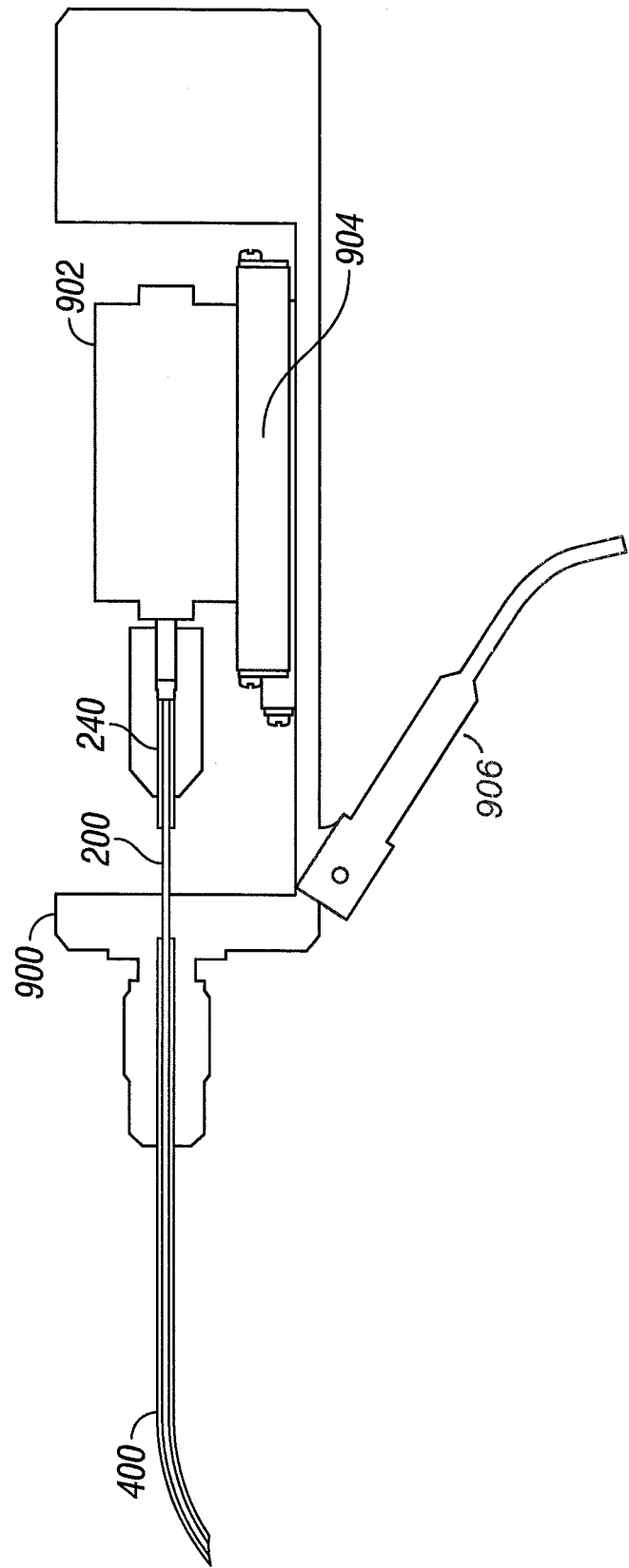
FIG. 11 is a view of drive unit which may be added to the directional drilling apparatus.

Referring to FIG. 11, the directional drilling apparatus 10 may be driven by a drill unit 900. The drive unit 900 may include a rotary motor 902 connected to the shaft 200, which may be via a drive tube 240, also depicted in FIG. 2. The rotary motor 902 operates at a fixed speed and is activated when control arm 906 is engaged. The operating speed of rotary motor 902 is sufficiently high to efficiently cut bone without burning. A control arm 906 associated with drive unit 900 may be moved through a range of positions, linearly causing a linear drive 904 to advance. The advance of linear drive 904 may be proportional to the movement of control arm 906. Control arm 906 may also be spring-loaded to cause linear drive 904 to retreat as control arm 906 is released. The linear drive 904 may be coupled to the shaft 200, which may be via a connection of the linear drive 904 to the rotary motor 902. Thus as the linear drive 904 advances and retreats by operation of control arm 906, shaft 200 likewise advances or retreats. Alternatively, the rotary motor 902 may be controllable through a number of rotational speeds, thus providing that the speed of the bit 100 (not illustrated in FIG. 7) may be controlled by the operator. Finally, the drive unit 900 may be coupled to the guide tube 400 to ensure control over the guide tube 400 and therefore the location drilled.

In either embodiment, the bit 100 drills through the bone 600 to provide for application of the medical treatment 700, as illustrated in FIG. 9 and FIG. 10. Once a passage 602 has been drilled through the bone 600, the medical treatment 700 may be introduced toward the cancerous lesion 603. The treatment 700 may be chemotherapy, radiotherapy, heat therapy or any other therapy known in the art. The amount of treatment 700 necessary for effective treatment may be far less than typically applied when given orally or introduced into the blood stream since the treatment 700 is introduced proximate the cancerous lesion 603. Likewise, the treatment 700 may be more effective as a result of directed application. As can be appreciated, the flow of the treatment 700 through the treatment delivery system 800 toward the cancerous lesion 603 is limited by the uptake of the treatment 700 by the cancerous lesion 603.

Alternatively, the treatment 700 may be directed toward the cancerous lesion 603 by a charge-driven application. Thus it may be possible to enhance the flow of the treatment 700 by applying a direct current potential between the treatment delivery system 800 and an electrode in conductive contact with the exterior of the limb placed as closely as possible to the region of the treatment delivery system 800. In one embodiment, a very fine liquid aerosol is generated and applied through electrostatic charging. In one embodiment, a liquid is passed through a nozzle, wherein a plume of droplets is generated by electrically charging the liquid to a very high voltage. The charged liquid in the nozzle becomes unstable as it is forced to hold more and more charge. Soon the liquid reaches a critical point, at which it can hold no more electrical charge and at the tip of the nozzle it blows apart into a cloud of tiny, highly charged droplets. These tiny droplets are particularly small, and fly about searching for a potential surface to land on that is opposite in charge to their own. Such droplets would be attracted to the cancerous lesion due to electrical differential. The apparatus may employ a sharply pointed hollow metal tube, such as a syringe needle, with liquid pumped through the tube. A high-voltage power supply may then be connected to the outlet of the tube and the tube positioned proximate a cancerous lesion 603. When the power supply is turned on and adjusted for the proper voltage, the liquid being pumped through the tube transforms into a fine continuous mist of droplets that fly rapidly toward the cancerous lesion 603.

Alternatively, if the treatment 700 consists of direct energy to be applied to the cancerous lesion 603, an optical tube sheathed in a metal, such as nickel, may be used to direct the treatment 700.

Additionally, via a passage 602, it is possible to visually observe cancerous lesion 603, such as with appropriately-sized fiber-optic or laparoscopic devices.

In operation, the drilling apparatus 10 is applied to or in close proximity to the bone 600 at the first end 401 of the guide tube 400. The shaft 200 and the bit 100 are rotated via rotation of the drive tube 240. Force is linearly applied to the shaft 200, which drives the bit 100 into the bone 600 and through the bone wall 601 to create a passage 602. Additionally, it is possible to direct the guide tube 400 against the bone 600 towards the cancerous lesion 603 from the opposite side of the cancerous lesion 603. The maximum penetration of the bit 100 into and through the bone 600 may be restricted by limiting the distance between the second end 403 of the guide tube 400 and the position of the drive tube 240. Alternatively, any stop having an outer diameter greater than the inner diameter 404 of the guide tube 400 may be affixed to the shaft 200.

The terms and expressions which have been employed in the foregoing specification are used therein as terms of description and not of limitation, and there is no intention, in the use of such terms and expressions, of excluding equivalents of the features shown and described or portions thereof.

We claim:

1. A device to penetrate living bone, comprising:
    a shaft,
        said shaft having a first end,
        said shaft being ductile;
    a cutting bit,
        said cutting bit formed at said shaft first end;
    a tubing jacket,
        said shaft slidably through said tubing jacket,
        said shaft being rotatable,
        said tubing jacket having an outer diameter,
        said tubing jacket having an inner diameter,
        said tubing jacket being as ductile as said shaft;
    a guide tube,
        said guide tube surrounding said tubing jacket and having a guide tube first end initially proximate said cutting bit,
        said tubing jacket slidably positioned for linear advancement toward said guide tube first end through said guide tube,
        wherein said guide tube is curved along its length at said guide tube first end,
        said guide tube adapted to bend said tubing jacket into a tubing jacket curvature during said linear advancement of said tubing jacket consistent to any curvature of said guide tube at said guide tube first end such that upon advancement of said tubing jacket through said guide tube first end and out of said guide tube, said tubing jacket will maintain said tubing jacket curvature imparted thereto by said guide tube; and
    a thrust bearing,
        said thrust bearing affixed and mounted to said shaft proximate said shaft first end intermediate said cutting bit and said tubing jacket,
        said thrust bearing having an outer diameter not greater than said tubing jacket outer diameter,
        said thrust bearing outer diameter being greater than said tubing jacket inner diameter.

2. The device of claim 1, wherein said tubing jacket inner diameter is approximately 0.0254 cm (0.010 inches).

3. The device of claim 2, wherein said tubing jacket has an interior finish to minimize friction.

4. The device of claim 3, wherein said shaft has a diameter of approximately 0.02286 cm (0.009 inches).

5. The device of claim 4, wherein
    said tubing jacket has a tubing jacket length, and
    said shaft has a length greater than said tubing jacket length.

6. The device of claim 5, wherein
    said cutting bit has a width,
        said cutting bit width greater than said tubing jacket outer diameter.

7. The device of claim 6 wherein
    said shaft and said tubing jacket are removable from said guide tube.

8. The device of claim 7, further comprising
    a second thrust bearing,
        said second thrust bearing affixed and mounted to said shaft adjacent said tubing jacket,
        said second thrust bearing having an outer diameter not greater than said tubing jacket outer diameter,
        said second thrust bearing outer diameter greater than said tubing jacket inner diameter.

9. The device of claim 1, further comprising
    at least one prong, said prong extending from said guide tube first end to a sharp end.

10. The device of claim 1, wherein
    said tubing jacket has a tubing jacket length, and
    said shaft has a length greater than said tubing jacket length.

11. The device of claim 10 wherein
    said cutting bit has a width,
        said cutting bit width greater than said tubing jacket outer diameter.

12. The device of claim 11, wherein
    a length of said guide tube is curved at said guide tube first end.

13. The device of claim 12 wherein
    said shaft and said tubing jacket are removable from said guide tube.

14. The device of claim 13 further comprising
    a second thrust bearing,
        said second thrust bearing affixed and mounted to said shaft adjacent said tubing jacket,
        said second thrust bearing having an outer diameter not greater than said tubing jacket outer diameter,
        said second thrust bearing outer diameter being greater than said tubing jacket inner diameter.

15. The device of claim 14, further comprising
    at least one prong, said prong extending from said guide tube first end to a sharp end.

16. The device of claim 15, further comprising
a drive unit, said drive unit including a rotary motor and a linear drive,
said rotary motor coupled to said shaft,
said linear drive coupled to said shaft,
said drive unit affixed to said guide tube.

17. The device of claim 16, further comprising
a control arm, said control arm coupled to said linear drive.

18. A method for drilling into living bone comprising:
applying a drill to the surface of said bone, said drill including
   a shaft,
      said shaft having a first end,
      said shaft being ductile;
   a cutting bit,
      said cutting bit formed at said shaft first end;
   a tubing jacket,
      said shaft slidably through said tubing jacket,
      said shaft being rotatable,
      said tubing jacket having an outer diameter,
      said tubing jacket having an inner diameter,
      said tubing jacket being as ductile as said shaft;
   a guide tube,
      said guide tube surrounding said tubing jacket and having a guide tube first end initially proximate said cutting bit,
      said tubing jacket slidably positioned for linear advancement toward said guide tube first end through said guide tube,
      wherein said guide tube is curved along its length at said guide tube first end,
      said guide tube adapted to bend said tubing jacket into a tubing jacket curvature during said linear advancement of said tubing jacket consistent to any curvature of said guide tube at said guide tube first end such that upon advancement of said tubing jacket through said guide tube first end and out of said guide tube, said tubing jacket will maintain said tubing jacket curvature imparted thereto by said guide tube; and
   a thrust bearing,
      said thrust bearing affixed to said shaft proximate said shaft first end intermediate said cutting bit and said tubing jacket,
      said thrust bearing having an outer diameter not greater than said tubing jacket outer diameter,
      said thrust bearing having an outer diameter greater than said tubing jacket outer diameter;
rotating said shaft,
applying said cutting bit to said bone,
cutting said bone, and
advancing said shaft, said bit and said tubing jacket from said guide tube into said bone.

19. The method of claim 18, wherein said guide tube includes a hypodermic needle section, and further comprising
withdrawing said shaft, said bit and said tubing jacket from said hypodermic needle section of said guide tube; and
inserting a capillary into said hypodermic needle section of said guide tube.

20. A device to penetrate living bone, comprising:
a shaft,
   said shaft having a first end,
   said shaft being ductile;
a cutting bit,
   said cutting bit formed at said shaft first end;
a tubing jacket,
   said shaft slidably through said tubing jacket,
   said shaft being rotatable,
   said tubing jacket having an outer diameter,
   said tubing jacket having an inner diameter,
   said tubing jacket being as ductile as said shaft;
a guide tube,
   said guide tube surrounding said tubing jacket and having a guide tube first end initially proximate said cutting bit,
   said tubing jacket slidably positioned for linear advancement toward said guide tube first end through said guide tube,
   wherein said guide tube is curved along its length at said guide tube first end,
   said guide tube adapted to bend said tubing jacket into a tubing jacket curvature during said linear advancement of said tubing jacket consistent to any curvature of said guide tube at said guide tube first end such that upon advancement of said tubing jacket through said guide tube first end and out of said guide tube, said tubing jacket will maintain said tubing jacket curvature imparted thereto by said guide tube; and
a thrust bearing,
   said thrust bearing affixed and mounted to said shaft proximate said shaft first end intermediate said cutting bit and said tubing jacket,
said thrust bearing having an outer diameter not greater than said tubing jacket outer diameter,
said thrust bearing outer diameter being greater than said tubing jacket inner diameter.

\* \* \* \* \*